United States Patent [19]

Gratzel et al.

[11] Patent Number: 5,223,634
[45] Date of Patent: Jun. 29, 1993

[54] MOLECULAR WATER OXIDATION CATALYST

[75] Inventors: Michael Gratzel, St. Sulpice, Switzerland; Shekhar Munavalli, Bel Air, Md.; Fu-Jann Pern; Arthur J. Frank, both of Lakewood, Colo.

[73] Assignee: The United States of America as represented by the United States Department of Energy, Washington, D.C.

[21] Appl. No.: 256,912

[22] Filed: Oct. 12, 1988

[51] Int. Cl.$^5$ .............................................. C07F 15/00
[52] U.S. Cl. ...................................... 556/137; 546/10
[58] Field of Search ........................... 556/137; 546/10

[56] References Cited

U.S. PATENT DOCUMENTS 3,081,357  3/1963  Alderson et al. .................... 260/635
3,804,914  4/1974  Fahey ............................. 260/666 A

OTHER PUBLICATIONS

Rotzinger, F. P., Munavalli, S., Comte, P., Hurst, J. K., Gratzel, M., Pern, F., and Frank, A. J., J. Am. Chem. Soc., vol. 109, No. 22, pp. 6619–6626 (1987).
Rotzinger, F. P., Munavalli, S., Comte, P., Hurst, J. K., and Gratzel, M., Chemical Abstracts, vol. 109, No. 10, Chem. Abst. No. 82008q, cited as ref. of Proceedings of the International Symposium on the Photochemistry and Photophysics of Coordination Compounds, held on Schloss Elmau, Fed. Rep. Ger., Mar. 29–Apr. 2, 1987.
Durham, B., Wilson, S. R., Hodgson, D. J., Meyer, T. J., J. Am. Chem. Soc. 1980, 102, p. 600.
Collin, J. P., Sauvage, J. P., Inorg. Chem. 1986, 25, p. 135.
Gersten, S. W., G. J. Samuels, T. J. Meyer, J. Am. Chem. Soc. 1982, 104, p. 4029.
Lay, P. S., W. H. F. Sasse, Inorg. Chem. 1985, 24, p. 4707.
Honda, K., A. J. Frank, J. Chem. Soc., Chem. Commun. 1984, p. 1635.
Gilbert, J. A., D. S. Eggleston, W. R. Murphy, D. A. Geselowitz, S. W. Gersten, D. J. Hodgson, T. J. Meyer, J. Am. Chem. Soc. 1985, 107, p. 3855.
Desilvestro, J. D. Duonghong, M. Kleijn, M. Gratzel, Chimia 1985, 39, 4, p. 102.
Frank, A. J., M. Gratzel, J. K. Hurst, F. Pern, Abstracts of Papers, 193rd ACS National Meeting, Am. Chem. Soc., Denver, Co., Apr. 5–10, 1987.

*Primary Examiner*—Paul F. Shaver
*Assistant Examiner*—Porfirio Nazario
*Attorney, Agent, or Firm*—James W. Weinberger; Thomas G. Anderson; William R. Moser

[57] ABSTRACT

A dimeric composition of the formula:

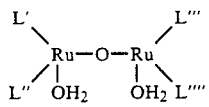

wherein L', L", L''', and L'''' are each a bidentate ligand having at least one functional substituent, the ligand selected from bipyridine, phenanthroline, 2-phenylpyridine, bipyrimidine, and bipyrazyl and the functional substituent selected from carboxylic acid, ester, amide, halogenide, anhydride, acyl ketone, alkyl ketone, acid chloride, sulfonic acid, phosphonic acid, and nitro and nitroso groups. An electrochemical oxidation process for the production of the above functionally substituted bidentate ligand diaqua oxo-bridged ruthenium dimers and their use as water oxidation catalysts is described.

3 Claims, 6 Drawing Sheets

MOLECULAR WATER OXIDATION CATALYST

BACKGROUND OF THE INVENTION

1. Field of the Invention

This invention relates to preparation of and water oxidation by functionally substituted bidentate ligand oxo-bridged ruthenium dimers. The dimer catalysts have high activity to catalyze oxygen evolution close to equilibrium conditions and provide good catalyst stability.

2. Description of the Prior Art

Catalysts for oxidation of water to molecular oxygen are critical in obtaining an energy efficient water splitting process. Various ruthenium complexes have been investigated in recent years as water oxidation catalysts.

Cis-trans photoisomerism and $ClO_4^-$ oxidation of $Ru(bpy)_2(OH_2)_2{}^+$ is taught by Durham, B., Wilson, S. R., Hodgson, D. J., Meyer, T. J., J. Am. Chem. Soc. 1980, 102, pg. 600. A number of mononuclear bis(diimine) complexes of ruthenium (II) were shown to have no activity toward the oxidation of water while the dinuclear $(bpy)_2(H_2O)RuORu(H_2O)(bpy)_2{}^{4+}$ was confirmed to be a catalyst for generation of $O_2$ from water. Collin, J. P.; Sauvage, J. P., Inorg. Chem. 1986, 25, pg. 135. Use of a catalyst of oxo-bridged dimeric system of ruthenium (III), $[(bpy)_2(H_2O)RuORu(H_2O)(bpy)_2]^{4+}$ is reported upon oxidation by four equivalents to provide rapid oxidation of water. Gersten, S. W., G. J. Samuels, T. J. Meyer, J. Am. Chem. Soc. 1982, 104, pg, 4029. Photochemistry of ruthenium complexes for water oxidation has been investigated using $[Ru(2,2'-bipyridine)_3]^{3+}$ with molecular oxygen evolution resulting from formation of binuclear oxo complexes which act as catalysts in the presence of $[Ru(bpy)_3]^{3+}$ for the oxidation of water to molecular oxygen. Lay, P. S. W. H. F. Sasse, Inorg. Chem. 1985, 24, pg. 4707. Photochemical catalytic oxidation of water in homogeneous media and in colloidal $SiO_2$ suspensions by the dimer $[(bpy)_2(H_2O)RuORu(H_2O)(bpy)_2]^{4+}$ is shown by Honda, K., A. J. Frank, J. Chem. Soc., Chem. Commun. 1984, pg. 1635. The redox properties of the water oxidation catalyst $[(bpy)_2(H_2O)RuORu(H_2O)(bpy)_2]^{4+}$ are taught by Gilbert, J. A., D. S. Eggleston, W. R. Murphy, D. A. Geselowitz, S. W. Gersten, D. J. Hodgson, T. J. Meyer, J. Am. Chem. Soc. 1985, 107, pg. 3855.

Oxygen generation under visible light illumination of highly acidic aqueous solutions of tris (2,2-bipryidine-4,4'dicarboxylic acid) ruthenium(II) containing $S_2O_8{}^{2-}$ as an electron acceptor in the absence of a heterogeneous redox catalyst is taught by Desilvestro, J., D. Duonghong, M. Kleiujn, M. Gratzel, Chimia 1985, 39, 4, pg. 102.

A water oxidation catalyst generated in situ from cis-$RuL_2(OH_2)_2$ where L=2,2'-bipyridine-5,5'-dicarboxylic acid is taught by A Molecular Water-Oxidation Catalyst, Frank, A. J., M. Gratzel, J. K. Hurst, F. Pern, Abstracts of Papers, 193rd ACS National Meeting, Am. Chem. Soc., Denver, Colo., Apr. 5-10, 1987. In this paper there was no disclosure of the dimeric form of the catalyst, electrochemical method for preparation of the catalyst, nor any disclosure of conditions required for water oxidation using the catalyst.

SUMMARY OF THE INVENTION

This invention relates to a dimeric composition having the general formula wherein L', L", L''', and L'''' are each a bidentate ligand having at least one functional substituent, said ligand selected from the group consisting of bipyridine, phenanthroline, 2-phenylpyridine, bipyrimidine, and bipyrazyl and said functional substituent selected from the group consisting of carboxylic acid, ester, amide, halogenide, anhydride, acyl ketone, alkyl ketone, acid chloride, sulfonic acid, phosphonic acid, and nitro and nitroso groups. One or both of the water molecules may be missing one or both of the hydrogens as shown in the above general formula, dependent upon the pH and the oxidation state of the metal. The general formula as used throughout this description and claims is meant to include this condition. This invention also relates to the process for preparation of the above diaqua functionally substituted bidentate ligand oxo-bridged ruthenium dimers by electrochemical oxidation of the monomeric diaqua precursor wherein ruthenium is in a 2+ oxidation state to the 3+ oxidation state followed by dimerization. This invention also includes use of the above identified diaqua functionally substituted bidentate ligand oxo-bridged ruthenium dimers as water oxidation catalysts in an oxidizing environment, including electrochemical, chemical and photochemical processes.

Preferred diaqua functionally substituted bidentate ligand oxo-bridged ruthenium dimers include those in which each functionally substituted bidentate ligand is 2,2'-bipyridyl-5,5'-dicarboxylic acid and/or 2,2'-bipyridyl-4,4'-dicarboxylic acid.

BRIEF DESCRIPTION OF THE DRAWING

The above mentioned and other features of the present invention, and the manner of obtaining them, will become apparent and the invention will be best understood by reference to the following description of preferred embodiments read in conjunction with the drawing wherein.

DESCRIPTION OF PREFERRED EMBODIMENTS

This invention relates to a dimeric composition of the formula wherein L', L'', L''', and L'''' are each a bidentate ligand having at least one functional substituent, the ligand being selected from the group consisting of bipyridine, phenanthroline, 2-phenylpyridine, bipyrimidine, and bipyrazyl and the functional substituent selected from the group consisting of carboxylic acid, ester, amide, halogenide, anhydride, acyl ketone, alkyl ketone, acid chloride, sulfonic acid, phosphonic acid, and nitro and nitroso groups. The functional substituents may be located at any substituent acceptable location on the ligand and may include any number of substituents which may be substituted on the particular ligand. In the case of a preferred bipyridine ligand, the functional substituent may be located at any one of the 3, 3' 4, 4', and 4, 5' positions and may have one substituent or may have two or more than two substituents. This invention is also meant to include both symmetrically substituted and unsymmetrically substituted bidentate ligands, such as in the case of bipyridyl ligand one pyridine moiety of the bipyridyl ligand substituted in for example the 3, position and the other in the 5' or 4' position. In preferred embodiments using the bipyridine ligand with carboxylic acid substituent, two substituent sites are suitable, namely 2,2'-bipyridyl-5,5'-dicarboxylic acid and 2,2'-bipyridyl-4,4'-dicarboxylic acid. It is known in the art or may be ascertained by known methods that certain substitution sites on certain of the bidentate ligands cannot be substituted with the functional substituents called for in the above formulation. Generally, from 1 to about 6 substituents are suitable, dependent upon the ligand, about 2 to about 4 being preferred.

The functionally substituted bidentate ligand oxo-bridged ruthenium dimers of this invention may be prepared by electrochemically oxidizing wherein L', L'', L''' and L'''' are each a bidentate ligand having at least one functional substituent as defined above to form the oxo-bridged dimeric product Specific examples using specific materials and conditions for 2,2'-bipyridine-5,5'-dicarboxylic acid substituted ligands is set forth in Examples I and II. The process set forth in Examples I and II uses $2.5 \times 10^{-3}$M cisRu$^{II}$L$_2$(H$_2$O)$_2{}^{2+}$ in 0.5 M H$_2$SO$_4$ aqueous solution under controlled potential electrolysis at 1.1 volts for 15 hours at 40° C., protected from light and purged with argon to remove H$_2$ to form sulfato complexes of the mixed valence dimer Ru$^{III}$-O-Ru$^{IV}$. The mixed valence dimer is electrolytically reduced at 0.65 volts to produce Ru$^{III}$-O-Ru$^{III}$ diaqua ligands which are separated by precipitation of monobarium salt. It will be apparent to one skilled in the art that other conditions may be suitable using different chemicals to produce the various dimeric compositions defined by the above formulas by the electrochemical process of this invention.

The controlled potential voltages, generally dependent upon the electrode materials, may be about 0.5 to about 2.0 V, preferably about 1.0 to about 1.2 V. Suitable temperatures for the electrochemical oxidation process of this invention may be about 0° to about 100° C., preferably about 30° to about 60° C. The electrochemical oxidizing may be carried out for about 5 to about 48 hours, largely dependent upon temperature, preferably about 10 to about 20 hours. The pH of the electrolyte solution may vary, largely, dependent upon the substituted ligand, and is generally low, in the order of about pH 0 to about pH 3.

Characterization and studies of the properties of a preferred functionally substituted bidentate ligand diaqua oxo-bridged ruthenium dimer according to this invention, wherein the substituted bidentate ligand is 2,2'-bipyridyl-5,5'-dicarboxylic acid is set forth more specifically in Examples III-V and similar properties of other dimeric compositions of the above formulation may be ascertained in the same fashion.

The functionally substituted bidentate ligand oxo-bridged diaqua ruthenium dimers of this invention are suitable catalysts for molecular water oxidation by contacting the molecular water under oxidation conditions with a catalytically effective amount of a dimeric composition of the formulation set forth above. By oxidative conditions we mean electrochemical oxidation environment as shown suitable in Example VI, chemical oxidation environment as shown suitable in Example VII and photochemical oxidation environment shown suitable in Example VIII. Examples VI-VIII specifically show water oxidation using the functionally substituted bidentate ligand oxo-bridged diaqua ruthenium dimers wherein the functionally substituted bidentate ligand are each 2,2'-dipyridyl-5,5'-dicarboxylic acid. The other dimeric compositions within the above dimeric formulation may be used for water oxidation catalysts in a similar fashion by cycling through various oxidation states.

Functionally substituted bidentate diaqua oxo-bridged dimers according to the above formulation wherein 2,2'-bipyridine-4,4'-dicarboxylic acid ligands were used have been prepared in substantially the same manner as described above for the 5,5' substituent. The 4,4' dicarboxylic acid position dimers also exhibit high activity for oxidation of water and generate oxygen by cycling through various oxidation states.

The following examples are set forth for further specific disclosure of preferred embodiments and are for the purpose of illustration only and not intended to limit the present invention in any way.

EXAMPLE I

Dimeric $L_2(H_2O)Ru$-$O$-$Ru(H_2O)L_2$, wherein L is 2,2'-bipyridyl-5,5'-dicarboxylic acid, was prepared in the following manner:

The ligand 5,5'-dicarbethoxy-2,2'-bipyridine, L', was prepared by dehydrogenative coupling of 30 g of ethyl nicotinate in the presence of 10 g of 10 percent Pd/charcoal (Fluka) under vacuum (15–20 mmHg) for five days at 125°–130° C. During filtration of the hot mixture, the crystalline solid separated. The crystals were washed with hexane and then extracted with toluene in a Soxhlet apparatus (27 percent yield; mp 145°–147° C.). The NMR of the compound was consistent with the assigned structure ($\delta$4.45, —$CH_2$; 1.42, —$CH_3$, both parts of the ethyl group; 8.59$\beta$H; 8.43$\gamma$H; 9.32$\alpha$H; solvent $CDCl_2$; internal standard $Me_4Si$). Also the IR spectrum was identical with that of an authentic sample.

The ruthenium (II) complex $RuL'_2Cl_2\cdot H_2O$ was prepared as follows: 390 mg (1.5 mmol) of $RuCl_3\cdot 3H_2O$ (Fluka, 38–40 percent Ru) and 900 mg (3mmol) of ligand L' were dissolved in 100 mL of absolute EtOH; the mixture was refluxed under an Ar atmosphere for 24 h. After cooling, 50 mL of 1 M LiCl as added and the EtOH was evaporated under reduced pressure. The crystals were filtered off, washed with $H_2O$, and then air-dried (yield: >90 percent). The complex was recrystallized from hot EtOH. Elemental analysis gave good agreement with the expected values (weight percentages calculated for $C_{34}H_{32}N_4O_8Cl_2Ru\cdot H_2O$ are quoted in parentheses): C, 48.56 (48.61); H, 4.46 (4.33); N, 7.04 (7.09); Cl, 8.93 (8.97); Ru, 12.70 (12.79).

The complex cis-$Ru^{II}L_2Cl_2.5H_2O$ was prepared by hydrolysis of $Ru^{II}L'_2Cl_2\cdot H_2O$; 200 mg (0.25 mmol) of the latter was dissolved in a 1:1 (v/v) mixture of ethanol and water to which 260 mg of triethylamine (BDH>99 percent) was added. The mixture was refluxed for 24 h. Subsequently, 2 g (ca. 20 mmol) of HCl (Fluka puriss, 37 percent) was added and the solution reduced in the rotavap to a small volume. The product was left to crystallize in the dark for 24 h. The crystals were filtered off and dried in vacuo (yield >90 percent). In air, this compound adds lattice water. Elemental analysis for $C_{24}H_{16}N_4O_8Cl_2Ru\cdot 2.5H_2O$ gave: C, 41.05 (40.86); H, 3.09 (3.00); N, 7.97 (7.94); Cl, 10.16 (10.05); Ru, 14.91 (14.84).

Stock solutions of cis-$Ru^{II}L_2(H_2O)_2^{2+}$ were prepared from $Ru^{II}L_2Cl_2$ in 0.5 M $H_2SO_4$ (Fluka puriss grade) of 1 M trifluoromethanesulfonic acid (Fluka purum p.a. grade, further purified by vacuum distillation). The chloride ligands in the $Ru^{II}$ complex were replaced by water ligands as follows. One mmole of silver sulfate (Fluka puriss.) was added to an $H_2SO_4$ solution of 1 mM $RuL_2Cl_2\cdot 2.5H_2O$; when $CF_3SO_3H$ was used as the solvent, 2 mmol of $AgCF_3SO_3$ (Fluka purum) was added. The solutions were heated for several hours to precipitate the chloride as AgCl. Subsequent filtration yielded the cis-$Ru^{II}L_2(H_2O)_2^{2+}$ solution that was used in the experiments. Care was taken to exclude light during this procedure and the stock solutions were stored in dark red bottles.

cis-$Ru^{II}L_2SO_4\cdot 4H_2O$ precipitates slowly (weeks) from a 0.5–1.0 M $H_2SO_4$ solution of $2.5\times 10^{-3}$ M cis-$Ru^{II}L_2(H_2O)_2^{2+}$. The black crystals were filtered and washed with water, a water-ethanol mixture, and pure ethanol, and then air-dried. Elemental analysis for $C_{24}H_{16}N_4O_{12}Ru\cdot 4H_2O$ yielded: C, 38.03 (38.05); H, 3.26 (3.19); N, 7.44 (7.40). The IR spectrum of the sulfato complex exhibited S-O stretching frequencies at 1037, 1100, and 1260 $cm^{-1}$. The latter is characteristic of bidentate chelation by $SO_2^{2-}$ and suggests that both cis-$Ru^{II}L_2(H_2O)_2^{2+}$ and $Ru^{II}L_2SO_4$ have a cis configuration since $SO_4^{2-}$ cannot coordinate to the trans isomer as a bidentate ligand. The assignment of the IR spectrum to the cis isomer concurs with spectrophotometric results.

The dimer $L_2(H_2O)Ru^{III}$-$O$-$Ru^{III}(OH_2)L_2$ ($1.25\times 10^{-3}$ M) was synthesized from a j0.5 M $H_2SO_4$ solution of $2.5\times 10^{-3}$ M cis-$Ru^{II}L_2(H_2O)_2^{2+}$ that was electrolyzed for 15 hours by controlled-potential electrolysis at 1.1 V using a Pt gauze electrode as follows. A 15-mL 0.5 M $H_2SO_4$ solution of $2.5\times 10^{-3}$ M $Ru^{II}L_2(H_2O)_2^{2+}$ was placed in a doubled-walled Pyrex cell connected to a thermostat adjusted to 40 ° C. The solution was protected from light to avoid cis-trans isomerization during the electrolysis. The cell was purged continuously with Ar to prevent reduction of the $Ru^{III}$ complex by hydrogen formed at the counter electrode.

At the end of the electrolysis, the color of the solution had changed from purple to red. The cyclic voltammogram, obtained with an In-doped $SnO_2$ working electrode (0.6 $cm^2$) with background current less than 1 $\mu$A throughout the potential range, shown in FIG. 1, exhibits a quasi-reversible wave centered at 680 mV (100-mV peak separation), a smaller reversible wave centered at 870 mV (60-mV peak separation), and the onset of a catalytic wave at potentials more positive than 1.35 V at a scan rate of 50 mV $s^{-1}$. These features are attributed to sulfato complexes of the mixed-valence dimer $Ru^{III}$-$O$-$Ru^{IV}$. (For convenience, the oxidation states of the dimer are denoted by formulas such as $Ru^{III}$-$O$-$Ru^{IV}$)

Upon reduction of the $Ru^{III}$-$O$-$Ru^{IV}$ dimer by electrolysis at 0.65 VC, the color of the solution changed from red to deep blue-green. The cyclic voltammogram of this solution (FIG. 2) is strikingly different from that obtained prior to reduction. The two principal features are a reversible wave at 0.98 V and a pronounced catalytic wave for oxygen production starting at 100–200 mV positive of the standard water-oxidation potential. There is also a shoulder on the cathodic part of the main wave at 870 mV. The corresponding anodic hump is barely visible. Furthermore, a very small wave centered at 0.6 V is discernible. The difference in the cyclic voltammograms obtained prior and subsequent to reduction are attributed to the replacement of sulfate by water ligands upon conversion of $Ru^{III}$-$O$-$Ru^{IV}$ to $Ru^{III}$-$O$-$Ru^{III}$.

The dimer was isolated from solution as follows. A 625 mL portion of 0.02 M $Ba(OH)_2$ was injected slowly into 25 mL of the dimer solution until the pH reached ca. 3.5. $BaSO_4$ was removed by filtration and the volume of the solution was reduced to 10 mL in a rotavap (bath temperature <50° C.). A second 625-mL aliquot of 0.02 M Ba$(OH)_2$ was added to this solution, lowering the pH to about 3.5. The volume was concentrated to 10 mL and the $BaSO_4$ was removed by filtration. Next, acetone was added slowly to the stirred solution at room temperature, resulting in the precipitation of the dimer as the monobarium salt. The solution was left in the dark for about 24 h. Dark blue crystals of the dimer were collected by filtration and washed with a 4:1 mixture of acetone and water. Elemental analysis of the crystals for $C_{48}H_{30}N_8O_{19}Ru_2Ba\cdot 13H_2O$ yielded: C, 36.78 (36.11); N, 7.01 (7.02); H, 3.9 (3.6). The carbon-to-nitrogen ratio of 6.12 (calculated value, 6.0) indicates that no decarboxylation took place during the preparation of the dimer. Infrared analysis of the crystals revealed the presence of both COOH and COO⁻ groups and the absence of sulfate.

EXAMPLE II

Figure 1:
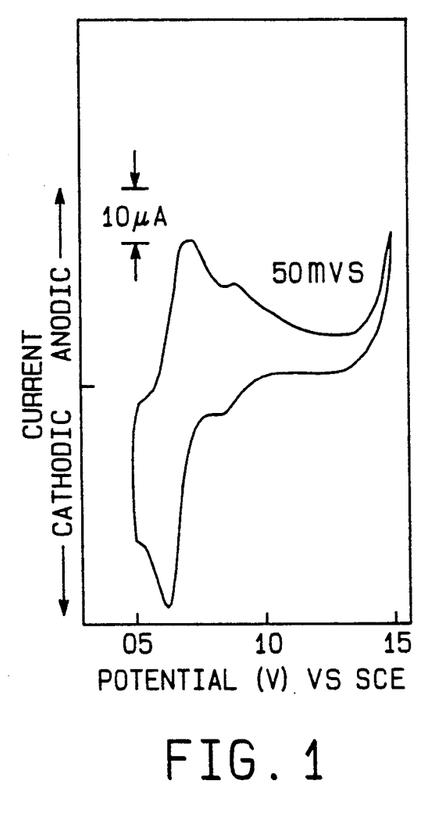
FIG. 1 is a cyclic voltammogram of the ruthenium oxo-bridged dimer sulfato complex as produced in Example I.
Figure 2:
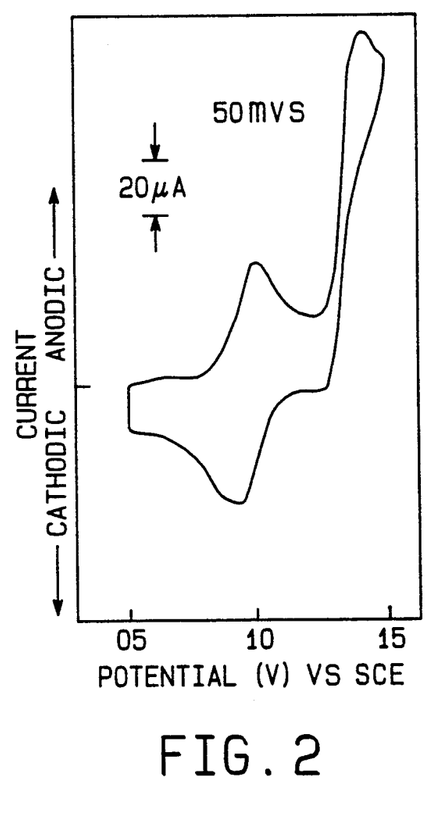
FIG. 2 is a cyclic voltammogram of the ruthenium oxo-bridged dimer with replacement of sulfate by water ligands as produced in Example I.
Figure 3:
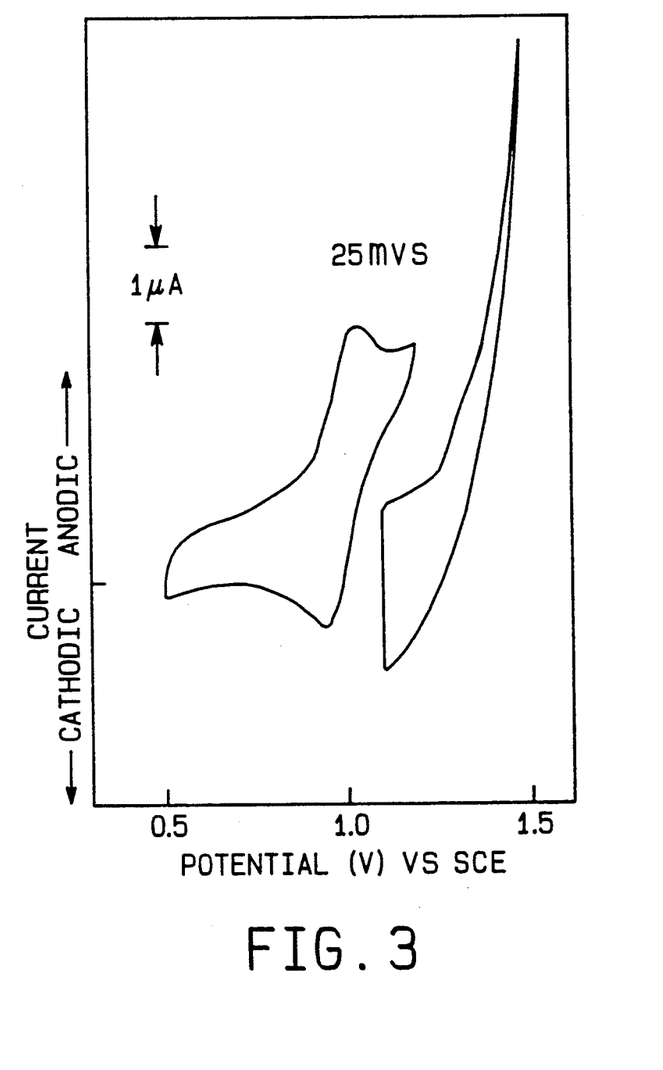
FIG. 3 are cyclic voltammograms of the oxidized and reduced forms of the dimer as set forth in Example II.

To confirm the basis for the cyclic voltammograms in FIGS. 1 and 2, the dimerization was performed with aqueous $CF_3SO_3H$ as the solvent: $10^{-3}$ M $Ru^{II}L_2(H_2O)_2^{2+}$ in 0.5 M $CF_3SO_3H$ was electrolyzed at 1.1 V and 25° C. for 24 h and then at 41° C. for another 24 h to complete the oxidative dimerization. At the end of electrolysis, the solution exhibited the characteristic red color of the $Ru^{III}$-O-$Ru^{IV}$ dimer which changed spontaneously within hours to the blue-green color of $Ru^{III}$-O-$Ru^{III}$. The current-voltage curves of the oxidized and reduced forms of the dimer were identical (FIG. 3). The cyclic voltammogram exhibits, apart from the catalytic wave, a reversible wave at E°=0.98 V, corresponding to the redox equilibrium between $Ru^{III}$-O-$Ru^{III}$ and $Ru^{IV}$-O-$Ru^{III}$ dimers.

Other waves that are observed in FIGS. 1 and 2 at lower potentials probably arise from dimers, whereon one or both water ligands have been replaced by sulfate or bisulfate. Complexes with different structures are possible since sulfate can coordinate to Ru as either a monodentate or a bidentate ligand. $Ru^{III}$-O-$Ru^{III}$ seems to coordinate sulfate much less strongly than $RuII^{III}$-O-$Ru^{IV}$, as is evident from the prominence of the 0.98-V wave in the cyclic voltammogram in FIG. 2. Presumably, the high electrophilicity of the Ru centers in the mixed-valence state favors sulfate coordination. The replacement of water ligands by sulfate in the mixed-valence dimer is a relatively slow process as shown by the following experiment.

Bulk electrolysis (at 1.1 V) of $Ru^{III}$-O-$Ru^{III}$ in 0.5 M $H_2SO_4$ quantitatively converts it back to the mixed-valence $Ru^{III}$-O-$Ru^{IV}$ state. The Faradaic charge passed during oxidation correlates with a one-electron process. If the oxidation is carried out sufficiently fast, for example, within about 1 h, the cyclic voltammogram of the $Ru^{III}$-O-$Ru^{IV}$ dimer is the same as that displayed in FIG. 2. Owing to the replacement of water by sulfate ligands, there is a slow change in the current-voltage curve upon maintaining the solution at a potential of 1.1 V. After two days, the features reverted to those shown in FIG. 1, indicating that sulfate coordination to $Ru^{III}$-O-$Ru^{IV}$ was complete. When this solution was again reduced at 0.65 V, the cyclic voltammogram shown in FIG. 2 was reproduced.

Similar to the behavior observed in aqueous $CF_3SO_3H$, the $Ru^{III}$-O-$Ru^{IV}$ dimer produced by rapid electrochemical or chemical oxidation of $Ru^{III}$-O-$Ru^{III}$ in aqueous 0.5 M $H_2SO_4$ undergoes spontaneous reduction back to the $Ru^{III}$-O-$Ru^{III}$ state within a few hours. When the dimer was maintained in the mixed-valence state for a longer period, e.g., by poising the solution potential at 1.1 V for several days, the spontaneous transformation of the III-IV state to the III-III state was no longer observed; the III-IV state appears stable for at least several months. Such stability can be rationalized in terms of the difference in the redox potentials between the diaqua and the sulfato complexes of the mixed-valence dimer. Freshly prepared, the mixed-valence dimer exhibits a standard redox potential of 0.98 V (FIG. 2). Upon aging for several days in 0.5 M $H_2SO_4$, sulfato complexes of the dimer are formed and the respective current maxima shift to 0.68 and 0.87 V, corresponding to those in FIG. 1. The lowering of the redox potential accounts for the increased stability of the aged dimer.

EXAMPLE III

Figure 4A:
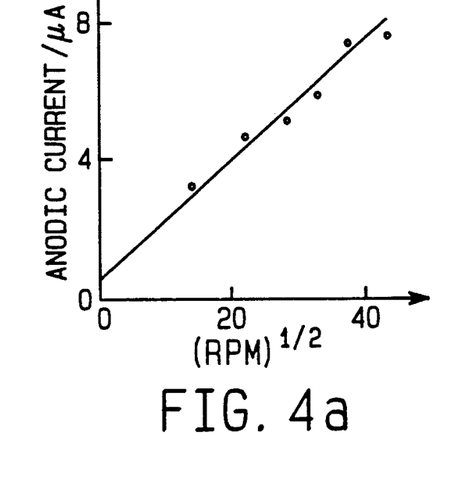
FIG. 4a is a plot of plateau current with the square root of the rotational speed of the dimeric complex set forth in Example III.
Figure 4B:
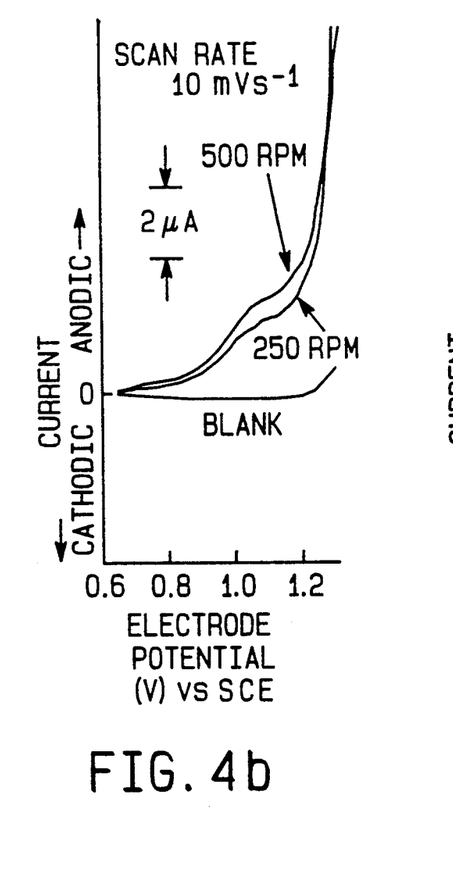
FIG. 4b is a current versus potential plot showing current has little dependence on rotational speed as described in Example III.
Figure 4C:
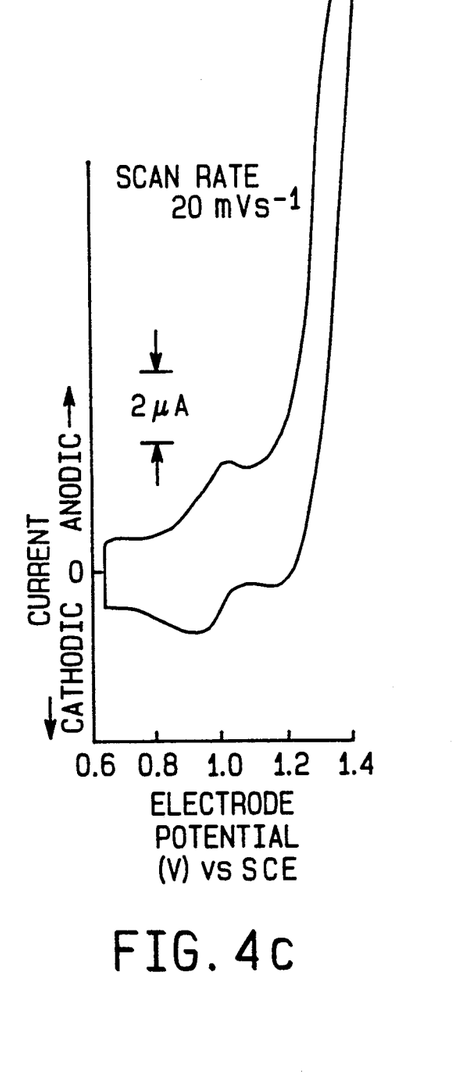
FIG. 4c is a cyclic voltammogram performed with a quiescent graphite electrode as described in Example III.

Characterization of the electrochemical properties of the dimeric complex $2.2\times10^{-4}$ M $L_2(H_2O)Ru$-O-$Ru(H_2O)L_2$ in 0.5 M $H_2SO_4$ was pursued using a rotating basal plane graphite disk electrode (0.2 cm²). FIG. 4b shows current-potential curves obtained at rotational speeds of 250 and 500 rpm, respectively. Two waves are clearly distinguishable. The first one has a halfwave potential of 0.98 V (vs. SCE) and the plateau current increases with the square root of the rotational speed in agreement with the Levich equation, FIG. 4a. Using a diffusion coefficient of $1.2\times10^{-6}$ cm⁻² s⁻¹ for the dimer, which corresponds to half of the value determined for the cis-Ru-$^{II}L_2(H_2O)_2^{2+}$ monomer, one electron is calculated to be transferred in the electrochemical reaction. This finding confirms that the reversible wave at 0.98 V is due to the one-electron oxidation of $Ru^{III}$-O-$Ru^{III}$ to produce the mixed-valence $Ru^{III}$-O-$Ru^{IV}$ dimer. FIG. 4b shows a steep increase in the anodic current at potentials positive to 1.1 V. In this potential domain, the current shows little dependence on the rotational speed, indicating that the wave corresponds to a catalytic process. The catalytic wave is also observed by cyclic voltammetry performed with the quiescent graphite electrode (FIG. 4c). The features of this voltammogram are the same as those observed with an In-doped $SnO_2$ electrode (FIG. 1). In particular, the reversible wave occurs at 0.98 V, corresponding to the one-electron oxidation of $Ru^{III}$-O-$Ru^{III}$ to produce the mixed-valence $Ru^{III}$-O-$Ru^{IV}$ dimer.

EXAMPLE IV

Figure 5A:
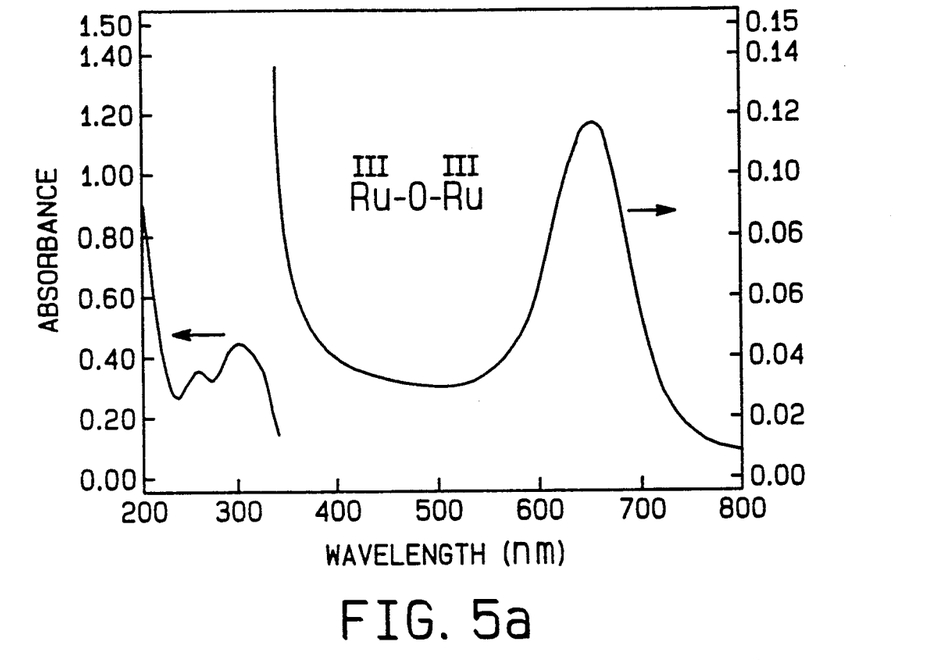
FIG. 5a is a plot f absorption spectrum of $Ru^{III}$-O-$Ru^{III}$ as described in Example IV.

The absorption spectrum of $3.3\times10^{-5}$ M $Ru^{III}$-O-$Ru^{III}$ in 0.5 M $H_2SO_4$ 0.2 cm optical path length is shown in FIG. 5a. It exhibits a strong symmetric absorption peak at 654 nm ($\epsilon 1.8\times10^4$ M⁻¹ cm⁻¹) in the visible region and two peaks at 257 nm ($\epsilon 5.5\times10^4$ M⁻¹ cm⁻¹) and 296 nm ($\epsilon 7\times10^4$ M⁻¹ cm⁻¹) in the ultraviolet region. The absorption spectrum is similar to that of the unsubstituted analogue, $[(bpy)_2(H_2O)Ru^{III}$-O-$Ru^{III}(H_2O)(bpy)_2]^{4+}$, except that all the maxima are red shifted with respect to the unsubstituted complex.

The $Ru^{III}$-O-$Ru^{III}$ dimer is cleaved by reductants such as ascorbic acid. When 90 μL of $10^{-2}$ M ascorbic acid in water was added to 100 μL of $1.25\times10^{-3}$ M $L_2(H_2O)Ru^{III}$-O-$Ru^{III}(H_2O)L_2$ in 0.5 M sulfuric acid, the solution turned purple within a few minutes and its spectrum was identical with that found for cis-$Ru^{II}L_2(H_2O)_2^{2+}$. Spectrophotometric analysis showed that the reductive cleavage of the dimer was quantitive:

The charge of $Ru^{III}$-O-$Ru^{III}$ is unspecified because the degree of protonation of the carboxyl groups of the dimer in aqueous 0.5 M $H_2SO_4$ is uncertain. The water ligands of $Ru^{III}$-O-$Ru^{IV}$ may also undergo deprotonation in 1 N acid. In the case of the unsubstituted analogues [(bpy)$_2$(H$_2$O)Ru$^{III}$-O-Ru$^{III}$(H$_2$O)(bpy)$_2$]$^{4+}$ and [(bpy)$_2$(H$_2$O)Ru$^{III}$-O-Ru$^{IV}$(H$_2$O)(bpy)$_2$]$^{5+}$, the water ligands undergo deprotonation above pH 6 and 0.4, respectively.

Figure 5B:
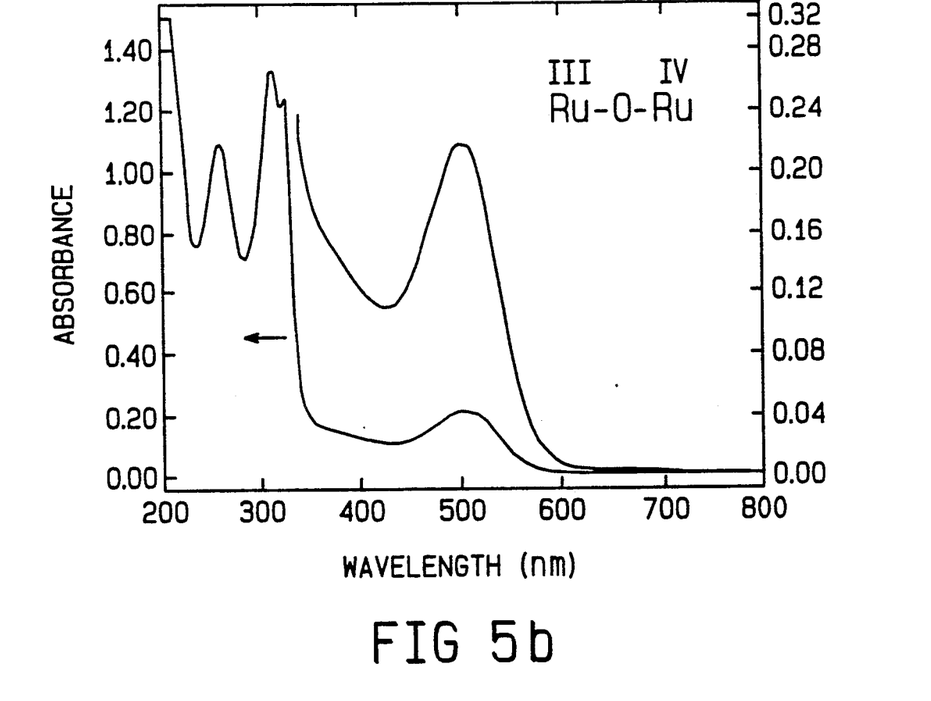
FIG. 5b is a plot of absorption spectrum of $Ru^{III}$-O-$Ru^{IV}$ as described in Example IV.

The UV-visible absorption spectrum of the mixed-valence dimer $1.3 \times 10^{-5}$ M Ru$^{III}$-O-Ru$^{IV}$ was obtained from a solution prepared by chemical oxidation of Ru$^{III}$-O-Ru$^{III}$ with Co$^{3+}$ ions in 0.5 M H$_2$SO$_4$. The cobaltic solution is particularly appropriate for spectral analysis since the absorption spectrum of both Co$^{3+}$ and CO$^{2+}$, at the concentrations employed, contribute negligibly to that of the dimer in the visible and UV regions of interest. A stock solution of cobaltic ions was prepared in 3 M H$_2$SO$_4$ by bulk electrolysis of $4 \times 10^{-2}$ M CoSO$_4$. Typically, 50 percent of the CO$^{2+}$ ions were oxidized to Co$^{3+}$ and the solution was stored under refrigeration. A 2-mL sample containing ca. $2 \times 10^{-5}$ M Ru$^{III}$-O-Ru$^{III}$ was mixed with the CO$^{3+}$, which was added in slight excess of the stoichiometric amount. Upon addition of Co$^{3+}$, the color of the solution changed immediately from blue-green to red. The absorption spectrum of the product, 1.0 cm optical path length, is shown in FIG. 5b having a symmetric peak at 500 nm in the visible region and peaks at 258, 313, and 325 nm in the UV region and is identified as that of the mixed-valence dimer Ru$^{III}$-O-Ru$^{IV}$. Similar to the situation of Ru$^{III}$-O-Ru$^{III}$, all the absorption maxima of Ru$^{III}$-O-Ru$^{IV}$ red shifted with respect to the unsubstituted analogue, [(bpy)$_2$(H$_2$O)Ru$^{II}$-O-Ru$^{IV}$(H$_2$O)(bpy)$_2$]$^{5+}$. The extinction coefficients of Ru$^{III}$-O-Ru$^{IV}$ were determined as $8.5 \times 10^4$ M$^{-1}$ cm$^{-1}$ (258) nm), $1 \times 10^5$ (313), $9.5 \times 10^4$ (325), and $1.7 \times 10^4$ (500). The replacement of water ligands by sulfate and/or bisulfate does not lead to large changes in the UV-visible spectrum of the mixed-valence dimer.

EXAMPLE V

Figure 6A:
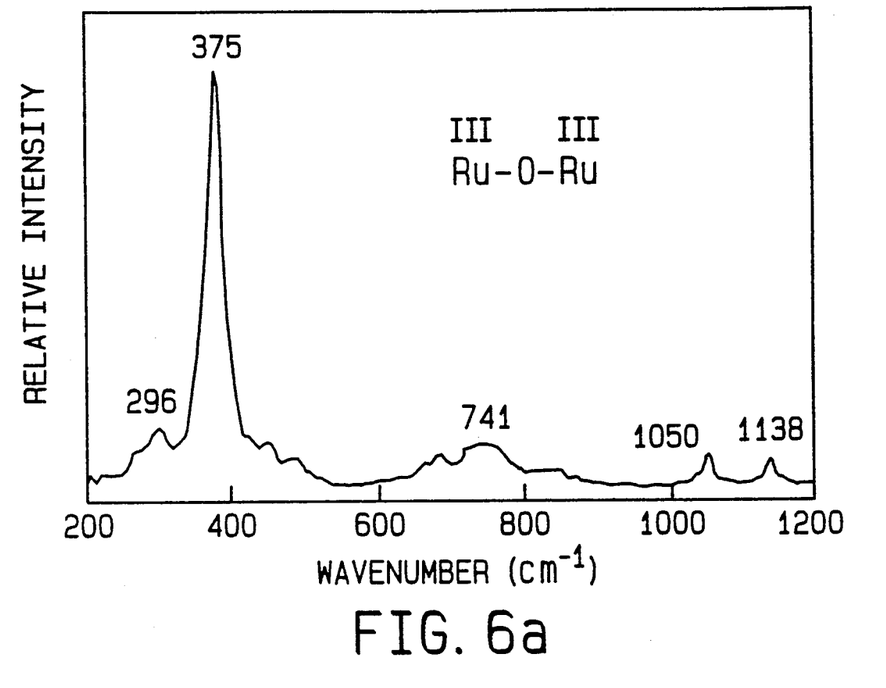
FIG. 6a is a plot of resonance spectrum of $Ru^{III}$-O-Ru-$^{III}$ as described in Example V.

Raman Spectra of Ru$^{III}$-O-Ru$^{III}$ and Ru$^{III}$-O-Ru$^{IV}$ in aqueous 0.5 M H$_2$SO$_4$ were recorded under both resonance and off-resonance conditions. The resonance spectrum of Ru$^{III}$-O-Ru$^{III}$, obtained from 647.1-nm excitation using a Kr ion laser at 40 mW power, 5 cm$^{-1}$ slit width, scan rate of 1 cm$^{-1}$ s$^{-1}$, background subtracted, average of two scans, 13-points smoothing routine, 90° scattering geometry shown in FIG. 6a, exhibits a single sharp peak at 375 cm$^{-1}$ and much smaller bands at 296, 741, 1050, and 1148 cm$^{-1}$. The off-resonance spectrum of Ru$^{III}$-O-Ru$^{III}$, obtained with 520.8-nm excitation, shows only a very weak feature in the 350–5090-cm$^{-1}$ region, indicating that the 375-cm$^{-1}$ line is resonance enhanced. Also the 375-cm$^{-1}$ line showed a polarization ratio of 0.33 which is the expected value for a resonance enhanced signal.

Figure 6B:
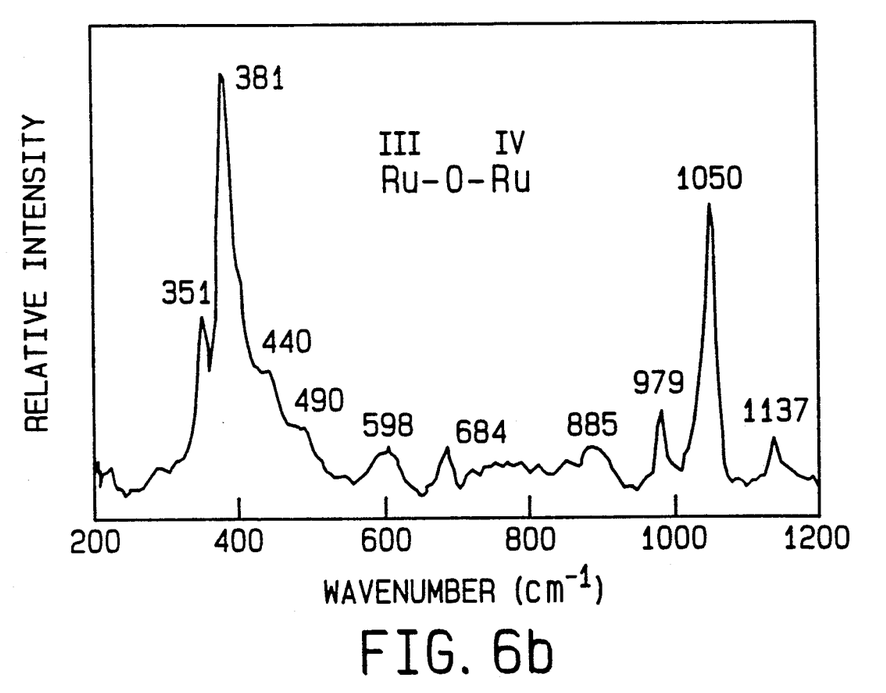
FIG. 6b is a plot of resonance spectrum of $Ru^{III}$-O-$Ru^{IV}$ as described in Example V.

On the basis of an extensive data base for oxo-bridged metal complexes, one can infer that the 350– to 500-cm$^{-1}$ wavenumber region corresponds to the Raman active M-O-M symmetric stretching frequency $v_s$. For example, $v_s$ (Fe-O-Fe) of ($\mu$-oxo)bis(aquobis(phenanthroline)iron (III)) occurs at 363 cm$^{-1}$. The feature of 375 cm$^{-1}$ is therefore assigned to the Raman-active (Ru-O-Ru) symmetric stretching frequency mode. One electron oxidation of Ru$^{III}$-O-Ru$^{III}$ by Ce$^{4+}$ to the mixed-valence dimer shifts this resonance line to 381 cm$^{-1}$ as illustrated in FIG. 6b. In the case of Ru$^{III}$-O-Ru$^{IV}$, resonance excitation was at 514.5 nm, using an Ar ion laser at 30 mW, single scan, 21-points smoothing with other conditions as described above. Other peaks in this spectrum are assigned to HSO$_4^-$ (1050, 885, 598 cm$^{-1}$), SO$_4^{2-}$ (979 cm$^{-1}$), and bipyridyl ligand modes (1137 cm$^{-1}$). The shoulder at 351 cm$^{-1}$ may be due to a fraction of Ru$^{III}$-O-Ru$^{IV}$ species which exists as a sulfato complex. These results confirm that the 650– and 500–nm absorption bands in FIG. 5 are due to $\mu$-oxo complexes.

Resonance Raman studies were also carried out on 0.5 M H$_2$SO$_4$ solutions of RuL$_3^{2+}$ with peroxodisulfate that had been illuminated by visible light or subject to thermolysis at 80° C. These studies provided unambiguous evidence for the formation of oxo-bridged ruthenium complexes. We assume that the dimers are formed via reactions:

$$H_2O + nH^+$$

Further oxidation of Ru$^{III}$-O-Ru$^{III}$ by peroxodisulfate to form Ru$^{III}$-O-Ru$^{IV}$ is also observed. The resonance Raman spectrum of product solutions showed at least four lines in the 350- to 500-cm$^{-1}$ wavenumber region, suggesting the formation of several Ru-O-Ru dimers with differing ligand composition and/or geometrical isomerism.

EXAMPLE VI

Electrochemical water oxidation using the dimeric L$_2$(H$_2$O)Ru-O-Ru(H$_2$O)L$_2$ as prepared in Example I was investigated. The cyclic voltammograms in FIGS. 1-4 show large catalytic waves with an onset that is 100-200 mV positive of the reversible electrode potential for oxygen evolution. The appearance of the high anodic current close to the thermodynamic threshold signifies efficient water-oxidation catalysis by the carboxylated ruthenium dimer. The kinetics for the catalytic oxidation of water with the carboxylated dimer are considerably more favorable than those with [(byp)$_2$(H$_2$O)Ru-O-Ru(OH$_2$)(bpy)$_2$]$^{4+}$. The latter system exhibits sluggish kinetics for O$_2$ production even at optimum pH conditions. At scan rates to 50 mV s$^{-1}$, [(bpy)$_2$(H$_2$O)Ru-O-Ru(OH$_2$)(bpy)$_2$]$^{4+}$ shows no catalytic wave for the oxidation of water on a glassy carbon electrode. In marked contrast, L$_2$(H$_2$O)Ru-O-Ru(OH$_2$)L$_2$ exhibits a catalytic wave for O$_2$ evolution from water at scan rates up to 2000 mV s$^{-1}$ (maximum sweep rate used) that suggests that the catalysis for O$_2$ production can occur in the millisecond-to-submillisecond time regime.

EXAMPLE VII

Chemical water oxidation using the dimeric L$_2$(H$_2$O)Ru-O-Ru(H$_2$O)L$_2$ as prepared in Example I was investigated. Dropwise addition of a mixture of $2 \times 10^{-2}$ M Co$^{3+}$ and $2 \times 10^{-2}$ M Co$^{2+}$ ions in 3 M H$_2$SO$_4$ to $2.5 \times 10^{-5}$ M L$_2$(H$_2$O)Ru$^{III}$-O-Ru$^{III}$(H$_2$O)L$_2$ in deaerated 1 M H$_2$SO$_4$ resulted in the immediate appearance of the characteristic red color in the mixed-valence dimer. The spectrum of Ru$^{III}$-O-Ru$^{IV}$ persisted even after the addition of a 300-fold stoichiometric excess of $Co^{3+}$. The excess $Co^{3+}$ ions were reduced rapidly to $Co^{2+}$ ions with simultaneous evolution of oxygen. The generation of oxygen was monitored quantitatively with a Clark-type $O_2$ sensor located in the head space of the cell. The production of $O_2$ was further cooroborated by gas chromatography. The reaction was terminated after about 1 hour. During this period, about 500 μL of $O_2$ had evolved. The amount of $O_2$ evolved and $Co^{3+}$ reduced corresponded to the stoichiometry of the reaction:

$$4Co^{3+} + 2H_2O \rightarrow O_2 + 4Co^{2+} + 4H^+$$

In the absence of the substituted Ru dimer, the reduction of $Co^{3+}$ by water is a slow process requiring many hours under the experimental conditions (1 M $H_2SO_4$ and 25° C.). Thus, a concentration of $2.5 \times 10^{-5}$ M Ru-O-Ru dimer is sufficient to accelerate markedly the water-oxidation reaction. The most striking aspect of this oxygen-evolution catalyst is its stability under the strongly oxidizing conditions prevailing in the acidic $Co^{3+/2+}$ solution, the electrochemical potential of which is about 1.5 V (vs. SCE). After complete conversion of $Co^{3+}$ to $Co^{2+}$ in the water-oxidation reaction, the turnover number of the Ru-O-Ru dimer was 75 was respect to $O_2$ production, and there were no signs of degradation. Specifically, the spectral features were unchanged and the absorbance of $Ru^{III}$-O-$Ru^{IV}$ at 500 nm remained within 10 percent of its original value; the spectrum was corrected for the contribution of $Co^{2+}$. This contrasts to the behavior of the unsubstituted dimer $[(bpy)_2(H_2O)Ru^{III}\text{-}O\text{-}Ru^{IV}(OH_2)(bpy)_2]^{5+}$ which was investigated under the same conditions. In the case of $[(bpy)_2(H_2O)Ru^{III}\text{-}O\text{-}Ru^{IV}(OH_2)(bpy)]_2^{5+}$, substantial irreversible spectral changes occurred during $O_2$ evolution, indicating degradation of this complex.

Oxygen evolution was also observed in 0.5 M $H_2SO_4$ solution containing $Ce^{4+}$ and small amounts of $Ru^{III}$-O-$Ru^{III}$. Upon addition of $2 \times 10^{-7}$ mol of $Ru^{III}$-O-$Ru^{III}$ to 10 mL of 0.1 M $(Ce(SO_4)_2$ in 0.5 M $H_2SO_4$, oxygen was generated at an initial rate of 40 μL $h^{-1}$. The rate declined to about 10 percent of this value after a few hours. This decrease was likely due to the slow replacement of water ligands in the mixed-valence dimer by sulfate and possibly due to complexation of the carboxyl groups of the bipyridyl ligands with $Ce^{3+}$. These sulfato complexes exhibit a much lower activity as oxygen-evolution catalysts than the dimer with aqua ligands and were essentially inactive in promoting water oxidation by 0.1 M $Ce(SO_4)_2$ in aqueous $H_2SO_4$. This observation is consistent with the current-voltage characteristics of these complexes in FIG. 1 which show a much smaller catalytic wave with an onset potential that is shifted positively by several hundred millivolts compared with that of the dimer with aqua ligands.

EXAMPLE VIII

Figure 7:
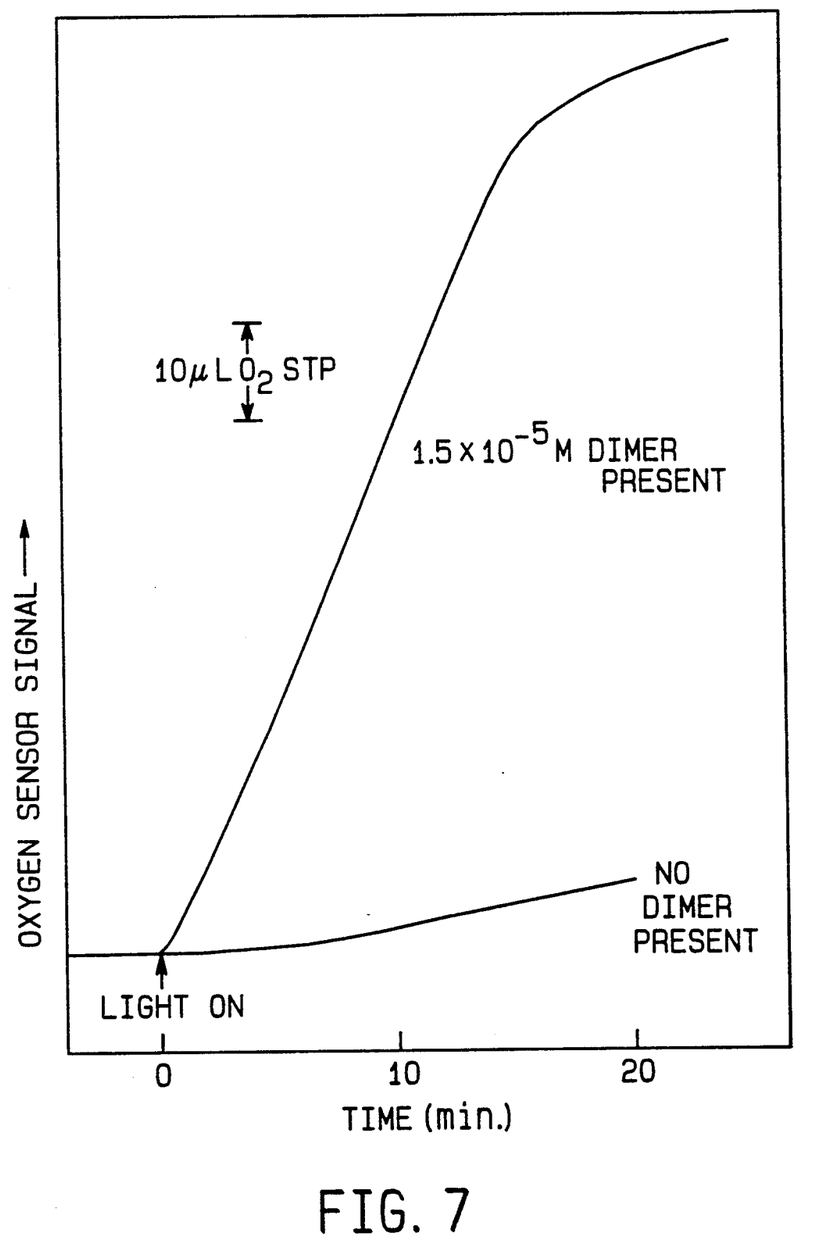
FIG. 7 is a plot of oxygen detected in visible light induced generation of oxygen as described in Example VIII.

Visible light induced generation of oxygen from water using the dimeric $L_2(H_2)Ru\text{-}O\text{-}Ru(H_2O)L_2$ as prepared in Example I was investigated. Visible-light irradiation in 10 mL aqueous 0.1 M phosphate buffer, pH 7, at 25° C. with $1 \times 10^{-4}$ M Ru(II) tris(4,4'-dicarbethoxy-2,2'-bipyridine) as a photosensitizer (S) and $5 \times 10^{-3}$ M $S_2O_8^{2-}$ as a sacrificial electron acceptor produces rapid and irreversible bleaching of the dye in the absence of the dimer. In striking contrast, sustained oxygen evolution is observed in the presence of $1.5 \times 10^{-5}$ M $Ru^{III}$-O-$Ru^{IV}$. FIG. 7 shows these $O_2$ production results. Oxygen is generated at a rate of 330 μL $h^{-1}$ during the first 15 minutes. Thereafter, the rate of production declines owing to the gradual depletion of the sensitizer. Spectrophotometric analysis indicated that the dimeric ruthenium complex is not degraded during this reaction. The mechanism for oxygen generation in this system involves photooxidation of the sensitizer by $S_2O_8^{2-}$ followed by water oxidation:

$$2S + S_2O_8^{2-} \xrightarrow{h\nu} 2SO_4^{2-} + 2S^+$$

$$2S^+ + H_2O \xrightarrow{Ru-O-Ru} 2H^+ + 2S + \tfrac{1}{2}O_2$$

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A dimeric composition of the formula:

wherein L', L'', L''', and L'''' are each a bidentate ligand 2,2'bipyridyl having at least one functional substituent in at least one of the positions selected from the group consisting of 3, 3', 4 and 4', and said functional substituent is carboxylic acid.

2. A dimeric composition according to claim 1 wherein L', L'', L''' and L'''' are each 2,2'-bipyridyl-4,4'-dicarboxylic acid.

3. A dimeric composition according to claim 1 wherein said substituent is at the 4, 4' positions.

* * * * *